United States Patent [19]

Colombo et al.

[11] Patent Number: 5,017,596

[45] Date of Patent: May 21, 1991

[54] ARYLPYRAZOLYLCARBINOL COMPOUNDS WITH ANALGESIC ACTIVITY

[75] Inventors: Augusto Colombo; Juan Pares both of Barcelone, Spain

[73] Assignee: Laboratorios del Dr. Esteve, S.A., Barcelona, Spain

[21] Appl. No.: 456,077

[22] Filed: Dec. 21, 1989

Related U.S. Application Data

[63] Continuation of Ser. No. 178,464, Apr. 7, 1988, abandoned.

[30] Foreign Application Priority Data

Apr. 10, 1987 [FR] France .................. 87 05118

[51] Int. Cl.$^5$ .................. C07D 231/16; A61K 31/415
[52] U.S. Cl. .................. 514/406; 548/374; 548/375; 548/378
[58] Field of Search .......... 548/378; 514/374, 375, 514/406

[56] References Cited

U.S. PATENT DOCUMENTS 4,213,994 7/1980 Gebert et al. .................. 548/327 X

FOREIGN PATENT DOCUMENTS 2137839 12/1972 France .................. 548/378
2166117 8/1973 France .................. 548/378

OTHER PUBLICATIONS

Synthesis, No. 9, Sep. 1978, pp. 675–676, Bastiaansen et al. "2-Aroylimidazoles: A Simple One-Step Synthesis".
Journal of Medical Chemistry, vol. 27, No. 12, Oct. 1984, pp. 1245–1253 Ashton et al., "Heterocyclic Analogs of Chlorcyclizine with Patent Hydrolipidemic Activity"-p. 1250.
Tetrahedron, vol. 39, No. 12, 1983, pp. 2023–2029-Katritzky et al. "Alpha-Lithiation of N-Alkyl Groups in Pyrazoles"-p. 2026.

Primary Examiner—Frederick E. Waddell
Assistant Examiner—Zinna Northington-Davis
Attorney, Agent, or Firm—Dressler, Goldsmith, Shore, Sutker & Milnamow, Ltd.

[57] ABSTRACT

The present invention relates to novel arylheteroarylcarbinol derivatives with analgesic activity and to their therapeutically acceptable salts.

These novel derivatives correspond to the general formula I:

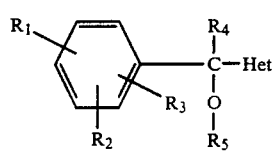

in which:

$R_1$, $R_2$ and $R_3$ represent a hydrogen atom, a halogen, a lower alkyl radical, a lower alkoxy radical or a trifluoromethyl group, $R_4$ represents a hydrogen atom, a $C_1$ to $C_4$ lower alkyl radical, a cycloalkyl, a lower alkenyl radical or a cycloalkylamino substituted on the nitrogen atom, $R_5$ represents a hydrogen atom or a radical of the formula:

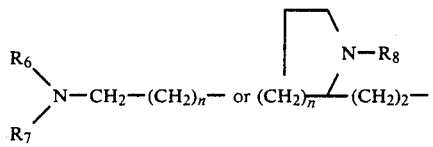

and
Het represents an azole.

7 Claims, No Drawings

ARYLPYRAZOLYLCARBINOL COMPOUNDS WITH ANALGESIC ACTIVITY

This application is a continuation of application Ser. No. 07/178,464, filed Apr. 7, 1988 now abandoned.

The present invention relates to novel arylheteroarylcarbinol derivatives, the method for their preparation and their application as drugs.

The compounds forming the subject of the present invention can also be used in the pharmaceutical industry as intermediates and for the preparation of drugs.

This type of carbinol has been studied very little and only a small number of examples are to be found in the scientific literature:

B. A. Tertov, *Khim.-Farm. Zh.*, 10, 34-6 (1976)
M. Ashton et al., *J. Med. Chem.*, 27, 1245-53 (1984)
S. Ohta et al., *Tetrah. Lett.*, 25, 3251-4 (1978)
L. A. M. Bastiaansen et al., *Synthesis*, 9, 675-6 (1978)
F. Effenberger, *J. Org. Chem.*, 49, 4687-95 (1984)
A. Katritzky, *Tetrahedron*, 39, 2023-9 (1983)
M. Okamoto, *Heterocycles*, 23 (7), 1759 (1985)

The novel arylheteroarylcarbinol derivatives forming the subject of the present invention correspond to the general formula (I):

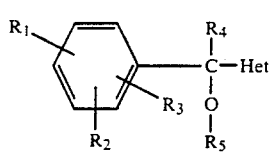

(I)

in which:
$R_1$, $R_2$ and $R_3$, which are identical or different, represent a hydrogen atom, a halogen, a lower alkyl radical, a trifluoromethyl group $CF_3$) or a lower alkoxy radical,
$R_4$ represents a hydrogen atom, a $C_1$ to $C_4$ lower alkyl radical, a cycloalkyl, a lower alkenyl radical or a cycloalkylamino radical substituted on the nitrogen atom,
$R_5$ represents a hydrogen atom or an aminoalkyl of the formula:

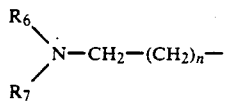

in which:
$R_6$ and $R_7$, which are identical or different, represent a lower alkyl, a cycloalkyl or a cycloalkoxy and n represents 1 or 2, or
$R_5$ represents a group of the general formula:

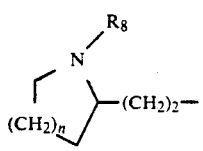

in which n can have the value 1 or 2 and $R_8$ represents a lower alkyl, and
Het represents an azole selected from:
(a) a pyrazole of the general formula:

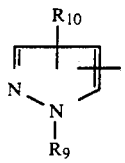

in which $R_9$ represents a hydrogen atom, a $C_1$ to $C_4$ lower alkyl radical, a dodecyl radical, a benzyl radical or a radical:

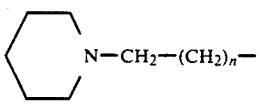

in which n=1 or 2, and $R_{10}$ represents a hydrogen atom, a methyl radical or a halogen atom,
(b) an imidazole of the general formula:

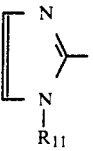

in which $R_{11}$ represents a hydrogen atom, a $C_1$ to $C_4$ lower alkyl radical, a benzyl radical, a dodecyl radical or a radical of the type:

$A-(CH_2)_n-$ in which n=2, 3 or 4 and A represents an N-piperidino radical, a cyano radical, a hydroxyl radical, a carboxyl radical, a carboxymethyl radical or an amino radical, and
(c) the imidazole of the formula:

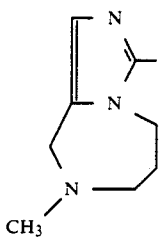

The present invention also relates to the physiologically acceptable salts of the compounds of the general formula, in particular the addition salts with physiologically acceptable mineral or organic acids, for example the oxalate, the tartrate, the citrate or the hydroquinonesulfonate.

The derivatives of the general formula I and their salts are suitable for preventing or treating pain of moderate to high intensity: sciatica, lumbago, dorsalgia, sprains, fractures and dislocations, all kinds of postoperative pain, pain of dental origin, etc.

The derivatives of the general formula I can also be used in the pharmaceutical industry as intermediates and for the preparation of drugs.

The novel derivatives of the general formula I can be prepared, according to the invention, by either one of the following methods:

Method A

Reaction of a compound of the general formula:

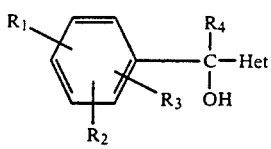

with a compound of the general formula:

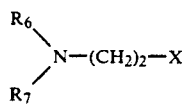

which formulae $R_1$ to $R_4$, $R_6$, $R_7$ and Het have the meanings mentioned above and X represents a halogen atom, preferably chlorine, or a leaving group selected from tosyloxy and mesyloxy.

The reaction of a compound of the general formula II with a compound of the general formula III is carried out in the presence of an appropriate solvent, for example a hydrocarbon such as benzene or toluene, or in a halogenated solvent such as methylene chloride or carbon tetrachloride, or in an ether such as tetrahydrofuran, or in another aprotic solvent such as dimethyl sulfoxide or dimethylformamide.

This reaction is advantageously carried out in the presence of an appropriate base such as an inorganic base like sodium or potassium hydroxide or sodium or potassium carbonate or bicarbonate.

This reaction is more advantageously carried out in the presence of a phase transfer catalyst such as tetrabutylammonium bromide, triethylbenzylammonium chloride or a crown ether, and within a temperature range between room temperature and the reflux temperature of the solvent.

Method B

Reaction of a compound of the general formula:

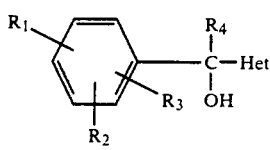

with a compound of the general formula:

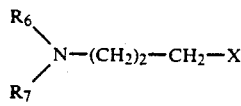

in which formulae $R_1$ to $R_4$, $R_6$, $R_7$, X and Het have the meanings mentioned above and X represents a halogen atom, preferably chlorine, or a leaving group selected from tosyloxy and mesyloxy.

The reaction of a compound of the general formula II with a compound of the general formula IV is carried out in the presence of an appropriate solvent, for example a hydrocarbon such as benzene or toluene, or in an ether such as tetrahydrofuran or dioxane. This reaction is advantageously carried out in the presence of an appropriate base such as an inorganic base like sodium or potassium hydroxide or sodium or potassium carbonate or bicarbonate.

This reaction is more advantageously carried out in the presence of a phase transfer catalyst such as tetrabutylammonium bromide, triethylbenzylammonium chloride or a crown ether.

This reaction can be carried out within a temperature range between 80° and 120° C.

The compounds of the general formula II can be prepared, according to the invention, by any one of the following methods:

Method C

Reduction of a compound of the general formula V:

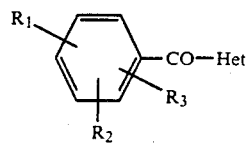

in which $R_1$, $R_2$, $R_3$ and Het have the meanings mentioned above, gives a compound of the general formula II in which $R_4$ is a hydrogen atom.

This reduction is carried out with a hydride such as lithium aluminum hydride, in an appropriate solvent such as an ether like tetrahydrofuran, dimethyl ether or dioxane, or with sodium borohydride in an alcohol such as methanol or ethanol, or with hydrogen and an appropriate catalyst such as Raney nickel, palladium or platinum oxide, in an appropriate solvent such as an alcohol, a cyclic hydrocarbon or an ether.

The pressure in the case of hydrogenation is advantageously between $10^5$ Pa and $10^6$ Pa, preferably between $10^5$ Pa and $2.10^5$ Pa, the most appropriate temperatures vary between 20° and 100° C. and the reaction time is between 1 hour and 48 hours.

Method D

Reaction of a compound of the general formula V with Grignard reagents of the type:

$R_{11}$—MgX in which $R_{11}$ represents a $C_1$ to $C_4$ lower alkyl, a substituted or unsubstituted $C_6$ cycloalkyl, a lower alkenyl or a substituted cycloalkylamino.

This reaction is carried out in an appropriate solvent, for example an ether such as diethyl ether, tetrahydrofuran or dioxane, or a mixture of these ethers with other solvents such as benzene, toluene or xylene.

Method E

Reaction of an aldehyde of the general formula:

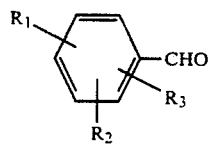

in which $R_1$, $R_2$ and $R_3$ have the meanings mentioned above, with the lithium salt of the azole, in an appropriate solvent such as ether or hexane. This reaction is preferably carried out at a temperature between $-15°$ C. and 100° C., preferably between $-5°$ C. and $+35°$ C.

Method F

Compounds of the formula:

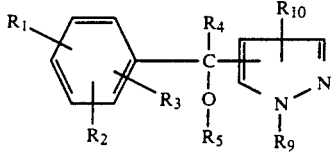

VII in which $R_1$, $R_2$, $R_3$, $R_4$, $R_5$ and $R_9$ have the meanings mentioned above and $R_{10}$ is chlorine or bromine, can be obtained by direct halogenation of the precursor compound.

Method G

Compounds of the formula:

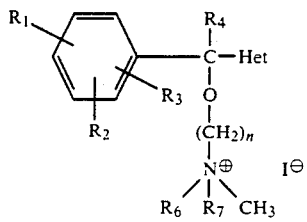

VIII are obtained from compounds of the formula I:

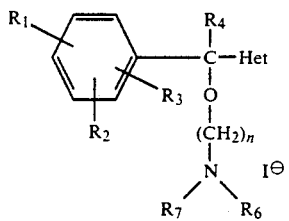

I in which $R_1$ to $R_7$ have the meanings mentioned above, by alkylation with methyl iodide, in an appropriate solvent such as a ketone like acetone or methyl ether ketone, at temperatures between room temperature and the reflux temperature of the solvent.

Method H

Compounds of the general formula IX:

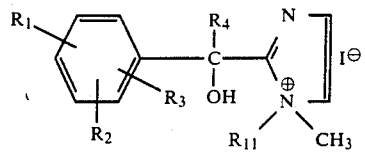

IX are obtained from compounds of the type:

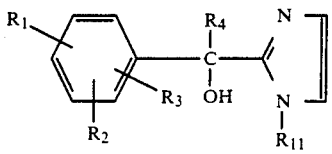

X in which formulae $R_1$ to $R_{11}$ have the meanings mentioned above, by reaction with methyl iodide.

This reaction is advantageously carried out in an appropriate solvent such as a ketone like methyl ethyl ketone or acetone, or an ether like dioxane, tetrahydrofuran or ether itself.

The preparation of novel derivatives according to the invention is indicated in the examples which follow. Some typical forms of use for the various fields of application will also be described.

The examples below are given simply by way of illustration and do not in any way limit the scope of the invention.

Method A (Examples 1 to 58)

Example no. 3:

Preparation of
α-(4-chlorophenyl)-1-methyl-0-(2-dimethylaminoethyl)
-1H-imidazole-2-methanol The following are introduced into a 500 ml conical flask:

20 ml of 5% NaOH,
100 ml of benzene,
2.2 g of α-(4-chlorophenyl)-l-methyl-1H-imidazole-2-methanol,
15 g of 2-(N,N-dimethylamino)chloroethane and
50 mg of benzyltriethylammonium chloride.

The mixture is stirred vigorously for 24 hours and left to stand and the organic phase is decanted and washed with water. It is dried over sodium sulfate and the solvent is removed in vacuo.

This gives 2.4 g (83%) of α-(4-chlorophenyl)-1-methyl -0-(2-dimethylaminoethyl)-1H-imidazole-2-methanol.

The compounds identified by Examples 1 to 58 are prepared by the same method of preparation as that described in Example 3 and the data for identification of the products are shown in Tables I to V.

TABLE I

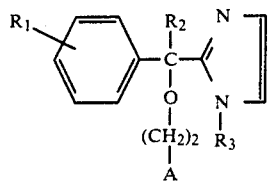

| Example n° | R₁ | R₂ | R₃ | A | Method |
|---|---|---|---|---|---|
| 1 | H | H | Me | DMA | A |
| 2 | 4 Cl | Me | Me | DMA | A |
| 3 | 4 Cl | H | Me | DMA | A |
| 4 | 3 Cl | H | Me | DMA | A |
| 5 | 2 Cl | Me | Me | DMA | A |
| 6 | 4 F | Me | Me | DMA | A |
| 7 | 3 F₃C— | Me | Me | DMA | A |
| 8 | 3 Cl | Me | Me | DMA | A |
| 9 | 3 Cl | n-Bu | Me | DMA | A |
| 10 | 4 Cl | Me | n-Bu | DMA | A |
| 11 | 4 MeO— | Me | Me | DMA | A |
| 12 | 3 Cl | Me | Me | Pyrr | A |
| 13 | 3 tri MeO— 4 5 | n-Bu | C₁₂H₂₅— | DMA | A |
| 14 | 4 F₃C— | H | n-Bu | DMA | A |
| 15 | 3 F₃C— | Me | Me | Pip | A |
| 16 | 3 di Cl 4 | cyclohexyl (H) | Me | DMA | A |
| 17 | 3 di Cl 4 | n-Bu | Me | DMA | A |
| 18 | 3 di Cl 4 | Me | Me | DMA | A |
| 19 | 3 di Cl 4 | H | Me | DMA | A |
| 20 | 4 Cl | Me | piperidino-N—(CH₂)₂— | DMA | A |
| 21 | 4 Cl | Me | piperidino-N—(CH₂)₃— | DMA | A |
| 22 | 4 Cl | H | N≡C—(CH₂)₃— | DMA | A |
| 23 | 4 Cl | Me-N-piperidinyl | Me | DMA | A |
| 24 | 4 Cl | H | —CH₂-phenyl | MBA | A |

DMA = dimethylamino
MBA = methylbenzylamine
Pyrr = pyrrolidine
Pip = piperidine

TABLE II

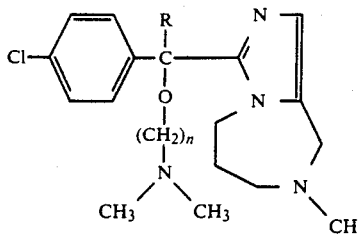

| Example n° | R  | n | Method |
|------------|----|----|--------|
| 25         | Me | 2 | A      |
| 26         | H  | 2 | A      |

TABLE III

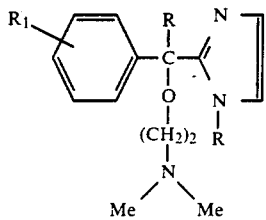

| Example n° | $^1$H NMR —Cl$_3$CD |
|---|---|
| 1 | 7,2 (s,5H); 6,8 (d,2H); 5,7 (s,1H); 3,5 (m,2H); 3,35 (s,3H); 2,6 (t,2H); 2,3 (s,6H) |
| 2 | 7,2 (s,4H); 6,85 (d,2H); 3,7 (m,1H); 3,2 (s,3H); 3,1 (m,1H); 2,5 (t,2H); 2,2 (s,6H); 1,85 (s,3H) |
| 3 | 7,25 (s,4H); 6,85 (d,2H); 6,65 (s,1H); 3,6 (m,2H); 3,45 (s,3H); 2,6 (t,2H); 2,25 (s,6H) |
| 4 | 7,3 (m,4H); 6,9 (d,2H); 5,7 (s,1H); 3,6 (m,2H); 3,5 (s,3H); 2,65 (t,2H); 2,35 (s,6H) |
| 5 | 7,9 (m,1H); 7,1 (m,3H); 6,8 (d,2H); 3,55 (m,1H); 3,05 (s,3H); 2,8 (m,1H); 2,4 (t,2H); 2,15 (s,6H); 2,0 (s,3H) |
| 6 | 7,0 (m,6H); 3,5 (m,2H); 3,3 (s,3H); 2,5 (t,2H); 2,3 (s,6H); 1,8 (s,3H) |
| 7 | 7,3 (m,3H); 6,8 (d,2H); 3,6 (m,2H); 3,2 (s,3H); 2,5 (m,2H); 2,2 (s,6H); 1,8 (s,3H) |
| 8 | 7,0 (m,3H); 6,8 (d,2H); 3,55 (m,2H); 3,2 (s,3H); 2,5 (m,2H); 2,2 (s,6H); 1,8 (s,3H) |
| 9 | 7,5-6,6 (m,6H); 3,55 (m,1H); 3,2 (s,3H); 3,0 (m,1H); 2,6 (m,2H); 2,2 (s,6H); 1,5-0,5 (m,7H) |
| 10 | 7,2 (s,4H); 6,9 (d,2H); 3,7 (m,3H); 3,0 (m,1H); 2,5 (t,2H); 2,25 (s,6H); 1,9 (s,3H); 1,4-0,6 (m,7H) |
| 11 | 7,0 (q,4H); 6,75 (d,2H); 3,7 (s,3H); 3,6 (m,1H); 3,25 (s,3H); 3,0 (m,1H); 2,55 (t,2H); 2,2 (s,6H); 1,9 (s,3H) |
| 12 | 7,1 (m,6H); 3,7 (m,1H); 3,2 (s,3H); 3,05 (m,1H); 2,7 (m,2H); 2,4 (m,4H); 1,9 (s,3H); 2,75 (m,4H) |
| 13 | 6,9 (d,2H); 6,5 (s,2H); 3,8 (s,3H); 3,7 (s,6H); 3,55 (m,1H); 3,0 (m,1H); 2,55 (t,2H); 2,2 (S,6H); 1,3-0,7 (m,34H) |
| 14 | 7,4 (s,4H); 6,8 (d,2H); 5,8 (s,1H); 3,6 (m,4H); 2,45 (t,2H); 2,1 (s,6H); 1,6-0,5 (m,7H) |
| 15 | 7,7 (s,1H); 7,35 (m,3H); 6,9 (d,2H); 3,7 (m,3H); 3,2 (s,3H); 3,1 (m,1H); 2,6 (m,2H); 2,4 (m,4H); 1,9 (s,3H); 1,45 (4H) |
| 16 | 7,5-6,7 (m,5H); 3,5 (m,1H); 3,1 (s,3H); 2,8 (m,2H); 2,4 (m,3H); 2,15 (s,6H); 2,0-0,3 (m,9H) |
| 17 | 7,5-6,7 (m,5H); 3,55 (m,2H); 3,20 (s,3H); 1,0 (m,1H); 3,5 (m,3H); 2,2 (s,6H); 1,4-0,6 (m,7H) |
| 18 | 7,4-6,7 (m,5H); 3,6 (m,2H); 3,20 (s,3H); 3,05 (m,2H); 2,5 (m,2H); 2,2 (s,6H); 1,8 (s,3H) |
| 19 | 7,6-6,7 (m,5H); 5,6 (s,1H); 3,6 (m,2H); 3,45 (s,3H); 2,6 (t,2H); 2,2 (s,6H) |
| 20 | 7,2 (s,4H); 6,95 (d,2H); 3,7 (m,3H); 3,0 (m,1H); 2,5 (t,2H); 2,2 (s,6H); 2,1 (m,6H); 1,8 (s,3H); 1,4 (m,6H) |
| 21 | 7,25 (s,4H); 6,9 (d,2H); 3,7 (m,3H); 3,1 (m,1H); 2,6 (t,2H); 2,20 (s,6H); 2,15 (m,6H); 1,9 (m,5H) |
| 22 | 7,3 (s,4H); 6,95 (d,2H); 5,7 (s,1H); 3,95 (m,4H); 3,6 (m,2H); 2,6 (t,2H); 2,2 (m,8H); 1,9 (m,2H); 1,45 (m,6H) |
| 23 | 7,3-6,7 (m,6H); 3,5 (m,1H); 3,1 (s,3H); 2,8 (m,4H); 2,4 (t,2H); 2,15-1,0 (m,19H) |
| 24 | 7,2 (s,12H); 7,0-6,8 (m,3H); 5,7 (s,1H); 5,0 (s,2H); 3,6 (m,2H); 3,5 (s,2H); 2,6 (t,2H); 2,2 (s,3H) |
| 25 | 7,25 (m,4H); 6,9 (s,1H); 4,0-3,0 (m,9H); 2,75 (m,2H); 2,55 (t,2H); 2,3 (s,6H); 1,9 (s,3H); 1,6-1,1 (m,3H) |
| 26 | 7,3 (s,4H); 6,8 (s,1H); 5,6 (s,1H); 4,5 (m,2H); 4,1-3,5 (m,8H); 2,8 (m,4H); 2,6 (t,2H); 2,2 (d,9H); 1,5 (m,3H) |

TABLE IV

| Example n° | $R_1$ | $R_2$ | $R_3$ | A | $R_4$ | Pyrazole substitution | Method |
|---|---|---|---|---|---|---|---|
| 27 | H | H | n-Bu | DMA | H | 5 | A |
| 28 | 4 Cl | 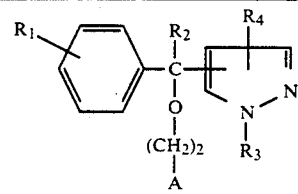 | Me | DMA | H | 5 | A |
| 29 | 3 tri MeO 4 5 | H | n-Bu | DMA | H | 5 | A |
| 30 | 4 Cl | Me | n-Bu | DMA | H | 5 | A |
| 31 | H | H | Me | DMA | H | 5 | A |
| 32 | H | Me | Me | DMA | H | 5 | A |
| 33 | 3 tri MeO | H | Me | DMA | H | 5 | A |

TABLE IV-continued

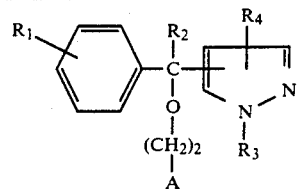

| Example n° | R₁ | R₂ | R₃ | A | R₄ | Pyrazole substitution | Method |
|---|---|---|---|---|---|---|---|
| 34 | H | H | Me | Pyrr. | H | 4, 5 | A |
| 35 | H | H | Me | Mor. | H | 5 | A |
| 36 | 3 tri MeO | Me | Me | DMA | H | 5 | A |
| 37 | H | H | Me | DMA | 4 Br | 4, 5 | A |
| 38 | H | Me | Me | DMA | 3 CH₃ | 5 | A |
| 39 | H | H | Me | DMA | 3 CH₃ | 5 | A |
| 40 | 2 Me | H | Me | DMA | H | 5 | A |
| 41 | 4 Cl | H | Me | DMA | 4 Cl | 5 | A |
| 42 | 4 Cl | H | Me | DMA | H | 4 | A |
| 43 | 4 Cl | Me | Me | DMA | H | 4 | A |
| 44 | 4 Cl | H | Me | DMA | H | 5 | A |
| 45 | 3 Cl | H | Me | DMA | H | 5 | A |
| 46 | 4 Me | H | Me | DMA | H | 5 | A |
| 47 | 2 Cl | H | Me | DMA | H | 5 | A |
| 48 | H | H | Me | Pip. | H | 5 | A |
| 49 | H | H | Me | N-Pr piperidine | H | 5 | A |
| 50 | 4 Cl | H | Me | N-Pr piperidine | H | 4 | A |
| 51 | H | H | Me | N-Et piperidine | H | 5 | A |
| 52 | H | H | Me | N-Me pyrrolidine | H | 5 | A |
| 53 | H | H | Me | DIPA | H | 5 | A |
| 54 | 4 Cl | H | Me | N-Me piperidine | H | 4 | A |
| 55 | 4 Cl | H | Me | N-Et piperidine | H | 4 | A |

TABLE IV-continued

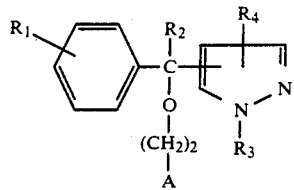

| Example n° | R₁ | R₂ | R₃ | A | R₄ | Pyrazole substitution | Method |
|---|---|---|---|---|---|---|---|
| 56 | H | H | Me | 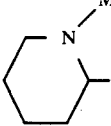 | H | 5 | A |
| 57 | 4 Cl | H | Me | DIPA | H | 4 | A |
| 58 | 4 Cl | H | Me | 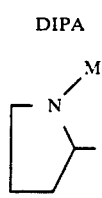 | H | 4 | A |

DIPA = diisopropylamine
Mor. = morpholine

TABLE V

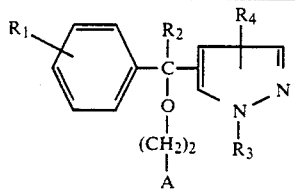

| Example n° | ¹H-NMR - Cl₃CD |
|---|---|
| 27 | 7,35 (m,6H); 5,95 (m,1H); 5,50 (s,1H); 4,05 (t,2H); 3,56 (t,2H); 2,52 (t,2H); 2,20 (s,6H); 1,75-0,7 (m,7H) |
| 28 | 7,5-7,1 (m,9H); 6,3 (d,1H); 3,45 (s,2H); 3,2 (t,2H); 2,55 (t,2H); 2,20 (s,6H) |
| 29 | 7,35 (m,1H); 6,6 (m,2H); 5,9 (t,1H); 5,45 (s,1H); 4,05 (t,2H); 3,8 (m,9H); 3,55 (t,2H); 2,6 (t,2H); 2,25 (d,6H); 1,9-0,7 (m,7H) |
| 30 | 7,45 (m,1H); 7,2 (s,4H); 6,3 (m,1H); 3,7 (t,2H); 3,15 (t,2H); 2,5 (t,2H); 2,25 (s,6H); 1,75 (s,3H); 1,65-0,6 (m,7H) |
| 31 | 7,2 (m,6H); 5,85 (d,1H); 5,35 (s,1H); 3,65 (s,3H); 3,4 (t,2H); 2,4 (t,2H); 2,1 (s,6H) |
| 32 | 7,45 (d,1H); 7,2 (s,5H); 6,4 (d,1H); 3,6 (m,1H); 3,4 (s,3H); 3,15 (m,1H); 2,55 (t,2H); 2,25 (s,6H), 1,8 (s,3H) |
| 33 | 7,35 (d,1H); 6,6 (s,2H); 6,0 (d,1H); 5,45 (s,1H); 3,85 (m,12H); 3,6 (t,2H); 2,6 (t,2H); 2,25 (s,6H) |
| 34 | 7,15-7,4 (m,6H); 5,9 (s,1H); 5,4 (s,1H); 3,65 (s,3H); 3,5 (t,2H); 2,65 (t,2H); 2,40 (m,4H); 1,65 (m,4H) |
| 35 | 7,3 (m,6H); 5,85 (d,1H); 5,4 (s,1H); 3,75 (s,3H); 3,55 (m,6H); 2,5 (t,2H); 2,35 (m,4H) |
| 36 | 7,45 (d,1H); 6,5 (s,2H); 6,35 (d,1H); 3,8 (s,3H); 3,75 (s,6H); 3,5 (s,3H); 2,5 (t,2H); 2,3 (s,6H); 1,8 (s,2H) |
| 37 | 7,45 (s,1H); 7,25 (s,5H); 5,85 (s,1H); 3,6 (m,5H); 2,6 (t,2H); 2,25 (s,6H) |
| 38 | 7,2 (m,5H); 6,15 (s,1H); 3,65 (m,1H); 3,35 (s,3H); 3,2 (m,1H); 2,5 (t,2H); 2,2 (s,9H); 1,75 (s,3H) |
| 39 | 7,25 (s,5H); 5,7 (s,1H); 5,45 (s,1H); 3,7 (s,3H); 3,5 (t,2H); 2,6 (b,2H); 2,25 (s,6H); 2,1 (s,3H) |
| 40 | 7,4-7,0 (m,5H); 5,7 (s,1H); 5,6 (s,1H); 3,85 (s,3H); 3,5 (t,2H); 2,55 (t,2H); 2,15 (s,9H); |
| 41 | 7,5-7,0 (m,6H); 6,1 (s,1H); 3,6 (m,5H); 2,7 (t,2H); 2,2 (s,6H) |
| 42 | 7,2 (s,5H); 7,0 (s,1H); 3,75 (s,3H); 3,35 (t,2H); 2,4 (t,2H); 2,1 (s,6H) |
| 43 | 7,2 (m,6H); 3,7 (s,3H); 3,25 (t,2H); 2,4 (t,2H); 2,15 (s,6H); 1,7 (s,3H) |
| 44 | 7,3 (m,5H); 5,9 (s,1H); 5,5 (s,1H); 3,8 (s,3H); 3,5 (t,2H); 2,5 (t,2H); 2,2 (s,6H) |
| 45 | 7,4-7,1 (m,5H); 6,0 (s,1H); 5,5 (s,1H); 3,8 (s,3H); 3,6 (t,2H); 2,6 (t,2H); 2,2 (s,6H) |
| 46 | 7,3 (s,1H); 7,2 (d,4H); 5,9 (s,1H); 5,4 (s,1H); 3,8 (s,3H); 3,5 (t,2H); 2,5 (t,2H); 2,3 (s,3H); 2,2 (s,6H) |
| 47 | 7,7-7,1 (m,5H); 5,9 (s,1H); 5,8 (s,1H); 3,9 (s,3H); 3,6 (t,2H); 2,5 (t,2H); 2,2 (s,6H) |
| 48 | 7,2 (s,6H); 5,8 (s,1H); 5,4 (s,1H); 3,7 (s,3H); 3,5 (t,2H); 2,5 (t,2H); 2,3 (m,6H); 1,4 (m,6H) |
| 49 | 7,4 (s,6H); 6,0 (s,1H); 5,4 (s,1H); 3,7 (s,3H); 3,6 (t,2H); 3,0-1 (m,5H); 0,9 (t,3H) |
| 50 | 7,3 (s,5H); 7,1 (s,1H); 5,2 (s,1H); 3,7 (s,3H); 3,45 (m,2H); 2,9-1,0 (m,17H); 0,8 (t,3H) |
| 51 | 7,3 (s,6H); 6,0 (s,1H); 5,4 (s,1H); 3,7 (s,3H); 3,5 (t,2H); 2,8-1,1 (m,13H); 1,0 (t,3H) |
| 52 | 7,3 (s,6H); 6,0 (s,1H); 5,4 (s,1H); 3,7 (s,3H); 3,5 (t,2H); 3,0 (m,1H); 2,2-1,0 (m,11H) |
| 53 | 7,3 (s,6H); 6,0 (s,1H); 5,5 (s,1H); 3,7 (s,3H); 3,4 (t,2H); 2,9 (m,2H); 2,6 (t,2H); 0,95 (d,12H) |
| 54 | 7,3 (s,5H); 7,1 (s,1H); 5,2 (s,1H); 3,8 (s,3H); 3,5 (t,2H); 2,7 (m,1H); 2,2 (m,3H); 2,1-1,0 (m,9H) |
| 55 | 7,3 (s,5H); 7,1 (s,1H); 5,3 (s,3H); 3,5 (t,2H); 2,8-1,1 (m,13H); 1,0 (t,3H) |
| 56 | 7,3 (s,6H); 6,0 (s,1H); 5,5 (s,1H); 3,8 (s,3H); 3,6 (t,2H); 2,8 (m,1H); 2,3 (s,3H); 2,2-1,1 (m,12H) |
| 57 | 7,3 (s,5H); 7,1 (s,1H); 5,3 (s,1H); 3,8 (s,3H); 3,4 (t,2H); 3,0 (m,2H); 2,7 (t,2H); 1,0 (d,12H) |
| 58 | 7,3 (s,5H); 7,1 (s,1H); 5,3 (s,1H); 3,8 (s,3H); 3,5 (m,2H); 3,0 (m,1H); 2,3 (s,3H); 2,2-1,2 (m,8H) |

Method B (Examples 59 to 104)

Example no. 59:

Preparation of α-(4-chlorophenyl -α-methyl-1-methyl-0-(3-dimethylaminopropyl) -1H imidazole-2-methanol The following are mixed, with vigorous stirring, in a 500 ml conical flask fitted with a condenser:
2.8 g of α-(4-chlorophenyl)-α-methyl-1-methyl-1H-imidazole-2-methanol,
3.8 g of 3-dimethylaminochloropropane,
80 ml of benzene,
20 ml of 50% NaOH and
50 mg of tetrabutylammonium bromide.

The mixture is refluxed for 24 hours and 3.8 g of 3-dimethylaminochloropropane are added.

The mixture is heated again for a further 24 hours and left to cool. The organic phase is decanted, washed several times with water and dried over sodium sulfate and the solvent is removed in vacuo.

This gives 3.0 g (86%) of α-(4-chlorophenyl)-α-methyl -1-methyl-0-(3-dimethylaminopropyl)-1H-imidazole-2-methanol.

The compounds identified by Examples 59 to 104 are obtained by the same method of preparation as that described in Example 59.

The data for identification of the products 59 to 104 are shown in Tables VI to VIII.

TABLE VI

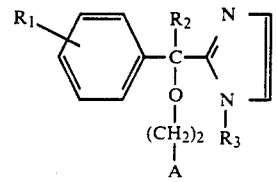

| Example n° | R₁ | R₂ | R₃ | A | Method |
|---|---|---|---|---|---|
| 59 | 4 Cl | Me | Me | DMA | B |
| 60 | 3 Cl | H | Me | DMA | B |
| 61 | 4 Cl | Et | Me | DMA | B |
| 62 | 3 Cl | n-Bu | Me | DMA | B |
| 63 | 4 Cl | ⌬H | Me | DMA | B |
| 64 | 4 F | Me | Me | DMA | B |
| 65 | 3 F₃C— | Me | Me | DMA | B |
| 66 | 2 Cl | Me | Me | DMA | B |
| 67 | 3 Cl | Me | Me | DMA | B |
| 68 | 3 tri MeO 4 5 | Me | Me | DMA | B |
| 69 | 4 MeO | Me | Me | DMA | B |
| 70 | 4 Cl | H | Me | DMA | B |
| 71 | 3 tri MeO 4 5 | H | Me | DMA | B |
| 72 | 4 F₃C— | Me | Me | DMA | B |
| 73 | 3 F₃C— | H | Me | DMA | B |
| 74 | 4 F₃C— | H | Me | DMA | B |
| 75 | 4 MeO— | H | Me | DMA | B |
| 76 | 3 F₃C— | n-Bu | Me | DMA | B |
| 77 | 4 Cl | Me | n-Bu | DMA | B |
| 78 | 3 tri MeO 4 5 | n-Bu | n-Bu | DMA | B |
| 79 | 2 Cl | n-Bu | n-Bu | DMA | B |
| 80 | 2 di Cl 4 | n-Bu | n-Bu | DMA | B |
| 81 | 4 F₃C— | H | n-Bu | DMA | B |
| 82 | 4 Cl | H | Me | Pip. | B |
| 83 | 4 F₃C— | Me | Me | Pip. | B |
| 84 | 2 Cl | n-Bu | Me | DMA | B |
| 85 | 3 di Cl 4 | n-Bu | Me | DMA | B |
| 86 | 3 di Cl 4 | Me | Me | DMA | B |
| 87 | 3 di Cl 4 | H | Me | DMA | B |
| 88 | 3 di Cl 4 | ⌬H | Me | DMA | B |

TABLE VI-continued

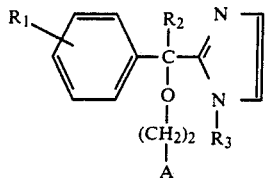

| Example n° | R₁ | R₂ | R₃ | A | Method |
|---|---|---|---|---|---|
| 89 | 4 Cl | Me | N-piperidinyl-(CH₂)₂— | DMA | B |
| 90 | 4 Cl | Me | N-piperidinyl-(CH₃)₃— | DMA | B |
| 91 | 4 Cl |  | CH₃—N-piperidinyl | Me | DMA | B |

TABLE VII

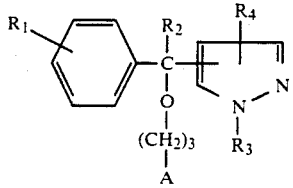

| Example n° | R₁ | R₂ | R₃ | A | R₄ | Pyrazole position | Method |
|---|---|---|---|---|---|---|---|
| 92 | H | H | n-Bu | DMA | H | 5 | B |
| 93 | 4 Cl | Me | n-Bu | DMA | H | 5 | B |
| 94 | H | H | Me | DMA | H | 5 | B |
| 95 | H | Me | Me | DMA | H | 5 | B |
| 96 | H | Me | Me | DMA | 3 Me | 5 | B |
| 97 | H | Me | Me | DMA | 3 Me | 5 | B |
| 98 | 2 Me | H | Me | DMA | H | 5 | B |
| 99 | 4 Cl | H | Me | DMA | H | 5 | B |
| 100 | H | H | Me | DMA | H | 4 | B |
| 101 | 4 Cl | H | Me | Mor. | H | 4 | B |
| 102 | 4 Cl | H | Me | Pyrr. | H | 4 | B |
| 103 | H | H | Me | Pip. | H | 5 | B |
| 104 | H | H | Me | Pyrr. | H | 5 | B |

TABLE VIII

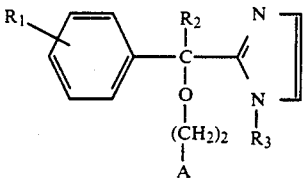

| Example no | ¹H NMR-Cl₃CD |
|---|---|
| 59 | 7,2(m,4H); 6,85(d,2H); 3,6(m,1H); 3,2(s,3H); 3,0(m,1H); 2,4(m,2H); 2,15(s,6H); 1,8(s,3H) |
| 60 | 7,2(s,1H); 7,15(s,3H); 6,8(d,2H); 5,6(s,1H); 3,55 (m,2H); 3,45(s,3H); 2,4(m,2H); 2,25(s,6H); 1,8(m,2H) |
| 61 | 7,2(s,4H); 6,8(d,2H); 3,4(m,3H); 3,1(s,3H); 2,9(m,1H); 2,3(m,2H); 2,2(s,6H); 1,8(m,2H); 0,5(t,3H) |
| 62 | 7,2(s,1H); 7,0(s,3H); 3,4(m,3H); 3,1(s,3H); 2,9(m,1H); |

TABLE VIII-continued

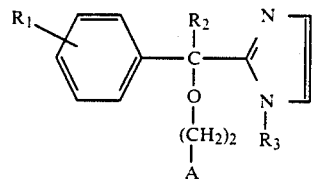

| Example no | ¹H NMR-Cl₃CD |
|---|---|
|  | 2,3(m,2H); 2,25(s,6H); 1,8(m,2H); 0,5(t,3H) |
| 63 | 7,15(s,4H); 6,8(d,2H); 3,5(m,1H); 2,7(m,1H); 2,4(m,4H); 2,5(s,6H); 1,9-0,5(m,14H) |
| 64 | 7,3-6,7(m,6H); 3,6(m,1H); 3,3(s,3H); 3,1(m,1H); 2,4 (m,2H); 2,25(s,6H); 1,9(s,3H); 1,85(m,2H) |
| 65 | 7,5(m,4H); 6,9(d,2H); 3,5(m,1H); 3,4(s,3H); 3,2(m,1H); 2,4(m,2H); 2,2(s,6H); 1,9(s,3H); 1,8(m,2H) |
| 66 | 8,0(m,1H); 7,2(m,3H); 6,8(d,2H); 3,6(m,1H); 3,1(s,3H); 2,8(m,1H); 2,3(m,2H); 2,2(s,6H); 2,0(s,3H); 1,7(m,2H) |
| 67 | 7,3-6,6(m,6H); 3,5(m,1H); 3,3(s,3H); 3,05(m,1H); 2,3 (m,2H); 2,15(s,6H); 1,9(s,3H); 1,8(m,2H) |
| 68 | 6,85(d,2H); 6,45(s,2H); 3,8(s,3H); 3,75(s,6H); 3,7 (m,1H); 3,3(s,3H); 3,0(m,1H); 2,4(m,2H); 2,25(s,6H); 1,9(s,3H); 1,8(m,2H) |
| 69 | 7,2-6,5(m,6H); 3,65(s,3H); 3,5(m,1H); 3,15(s,3H); 2,9 (m,1H); 2,3(m,2H); 2,15(s,6H); 1,85(s,3H); 1,8(m,2H) |
| 70 | 7,25(s,4H); 6,85(d,2H); 5,65(s,1H); 3,5(m,2H); 3,40 (s,3H); 2,35(m,2H); 2,2(s,6H); 1,8(m,2H) |
| 71 | 6,8(d,2H); 6,55(s,2H); 6,6(s,1H); 3,75(s,9H); 3,55 (m,2H); 3,45(s,3H); 2,3(m,2H); 2,2(s,6H); 1,8(m,2H) |
| 72 | 7,4(q,4H); 6,85(d,2H); 3,6(m,1H); 3,25(s,3H); 3,0 (m,1H); 2,4(m,2H); 2,25(s,6H); 1,9(s,3H); 1,8(m,2H) |
| 73 | 7,6(s,1H); 7,4(s,2H); 6,8(d,2H); 6,7(s,1H); 3,6(m,2H); 3,4(s,3H); 2,4(m,2H); 2,15(s,6H); 1,9(m,2H) |
| 74 | 7,5(q,4H); 6,85(d,2H); 5,65(s,1H); 3,55(m,2H); 3,45 (s,3H); 2,4(m,2H); 2,25(s,6H); 1,8(m,2H) |
| 75 | 7,3-6,7(m,6H); 5,7(s,1H); 3,8(s,3H); 3,65(m,2H); 3,55 (s,3H); 2,4(m,2H); 2,25(s,6H); 1,9(m,2H) (m,7H) |
| 76 | 7,6(s,1H); 7,4(m,3H); 6,8(d,2H); 3,5(m,1H); 3,2(s,3H); 2,9(m,1H); 2,4(m,2H); 2,25(s,6H); 1,9(m,2H); 1,5-0,5 (m,7H) |
| 77 | 7,2(s,4H); 6,9(d,2H); 3,6(m,3H); 3,0(m,1H); 2,3(m,2H); 2,2(s,6H); 1,9(s,3H); 1,7(m,2H); 1,5-0,5(m,7H) |
| 78 | 6,8(d,2H); 6,4(s,2H); 3,75(s,3H); 3,65(s,6H); 3,6 (m,9H); 3,6-2,5(m,6H); 2,2(s,6H); 1,6-0,4(m,16H) |

TABLE VIII-continued

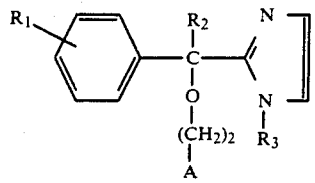

| Example no | $^1$H NMR-Cl$_3$CD |
|---|---|
| 79 | 7,9(m,1H); 7,15(m,3H); 6,8(d,2H); 3,45(m,2H); 3,0-2,2 (m,4H); 2,2(s,6H); 2-0,5(m,18H) |
| 80 | 7,9(m,1H); 7,4(m.2H); 6,8(dd,2H); 3,4(m,3H); 2,7(m,2H); 2,3(m,3H); 2,1(d,6H); 1,9-0,5(m,16H) |
| 81 | 7,4(q,4H); 6,8(d,2H); 5,6(s,1H); 3,5(m,4H); 2,2(m,2H); 2,05(s,6H); 1,8-0,5(m,9H) |
| 82 | 7,3(s.4H); 6,9(d,2H); 5,6(s,1H); 3,4(m,5H); 2,45(m,6H); 2-12(m,8H) |
| 83 | 7,4(q,4H); 7,85(d,2H); 3,6(m,1H); 3,2(s,3H); 3,0(m,1H); 2,3(m,6H); 1,9(s,3H); 1,4(m,8H) |
| 84 | 8.0(d,1H); 7,2(m,3H); 6,8(d,2H); 3,4(m,1H); 3,0(s.3H); 2,8(m,1H); 2,3(m,4H); 2,15(s,6H); 1,8-0,5(m,9H) |
| 85 | 7,4-6,6(m,5H); 3,4(m,1H); 3,2(s,3H); 2,9(1H); 2,3 (m,4H); 2,15(s,6H); 1,9-0,5(m,2H) |
| 86 | 7,3(m,2H); 6,8(m,3H); 3,6(m,1H); 3,2(s,3H); 2,9(m,1H); 2,3(m,4H); 2,2(s,3H); 1,8(s,3H) |
| 87 | 7,5-6.9(m,3H); 6,8(d,2H); 5,6(s,1H); 3,5(m,2H); 3,4 (s,3H); 2,3(m,2H); 2,1(s,6H); 1,8(m,2H) |
| 88 | 7,6-6,7(m,5H); 3,4(m,1H); 2,7(m,1H); 2,4(m,4H); 2,15 (s,6H); 1,9-0,3(m,14H) |
| 89 | 7.1(s,4H); 6,95(s,1H); 6,85(s,1H); 3,6(m,4H); 2,3 (m,4H); 2,1(s,6H); 2,05(m,4H); 1,8(m,6H); 1,3(m,8H) |
| 90 | 7,2(s,4H); 6,9(s,1H); 6,85(s,1H); 3,6(m,4H); 2,3(m,4H); 2,1(s,6H); 2,05(m,4H); 1,8(m,6H); 1,4(m,10H) |
| 91 | 7,2-6.6(m,6H); 3,4(m,1H); 3,1-2,5(m,8H); 2,5-1,5(m,14H); 1,0(m,4H) |
| 92 | 7,25(m,6H); 5,9(m,1H); 5,4(s,1H); 3,95(t,2H); 3,40 (t,2H); 2,25(t,2H); 2.1(s,6H); 1,85-0,5(m,9H) |
| 93 | 7,45(d,1H); 7,2(s,4H); 6,3(d,1H); 3,8(m,3H); 3,1(m,1H); 2,35(t,2H); 2,15(s,6H); 1,8(s,3H); 1,9-0,6(m,9H) |
| 94 | 7,3(s,6H); 5,95(d,1H); 5,45(s,1H); 3,75(s,3H); 3,5 (t,2H); 2,35(t,2H); 2,15(s,6H); 1,8(m,2H) |
| 95 | 7,4(d,1H); 7,2(s,5H); 6,35(d,1H); 3,55(m,2H); 3,4 (s,3H); 2,35(t,2H); 2,2(s,6H); 1,95-1,6(m,5H) |
| 96 | 7,15(s,5H); 6.0(s,1H); 3,4(m,1H); 3,25(m,3H); 3,0 (m,1H); 2,2(m,11H); 1,6(m,5H) |
| 97 | 7,3(s,5H); 5,75(s,1H); 5,35(s,1H); 3,7(s,3H); 3,45 (t,2H); 2,35(t,2H); 2,15(s,9H); 1,75(m,2H) |
| 98 | 7,4-7,1(m,5H); 5,7(s,1H); 5,5(s,1H); 3,8(s,3H); 3,5 (t,2H); 2,3(m,2H); 2,2(s,9H); 1,8(m,2H) |
| 99 | 7,4-7,2(m,5H); 5,9(s,1H); 5,4(s,1H); 3,7(s,3H); 3,5 (t,2H); 2,3(m,2H); 2,15(s,6H); 1.8(m,2H) |
| 100 | 7,3(b,6H); 7,1(s,1H); 5,3(s,1H); 3,7(b,3H); 3,7-3,3 (m,2H); 2,3(m,2H); 2,2(b,6H); 1,8(m,2H) |

TABLE VIII-continued

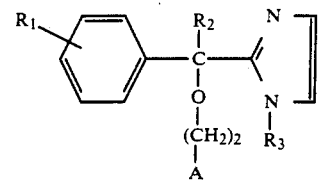

| Example no | $^1$H NMR-Cl$_3$CD |
|---|---|
| 101 | 7,3(b,5H); 7,1(s,1H); 5,2(s,1H); 3,8(s,3H); 3,6(m,6H); 2,4(m,6H); 1,9(m,2H) |
| 102 | 7,3(b,5H); 7.1(s.1H); 5,3(s.1H); 3,8(s,3H); 3,5(m,2H); 2,5(m,6H); 1,8(m,6H) |
| 103 | 7,3(s,6H); 6,0(s,1H); 5,4(s,1H); 3,7(s,3H); 3,5(t,2H); 2,3(m,6H); 1,9(m,2H); 1,5(m,6H) |
| 104 | 7,3(b.6H); 6,0(b,1H); 5,4(s,1H); 3,7(s,3H); 3,6(m,2H); 2,5(m,6H); 1,8(m,6H) |

Method C (Examples 105 et seq.)

Example 110:

Preparation of 1-methyl-α-(3-trifluoromethylphenyl)-1H-imidazole-2-methanol 0.6 g of sodium borohydride is added to a solution of 3.6 g of 1-methyl-α-(3-trifluoromethylphenyl)-1H-imidazole-2-methanone in 25 ml of methanol. The mixture is stirred for 30 minutes and 150 ml of water are added. The precipitate obtained is filtered off and washed with water. It is recrystallized from an ethanol/water mixture.

This gives 3.2 g (58%) of white crystals melting at 125°-6° C., which correspond to 1-methyl-α-(3-trifluoro-methylphenyl)-1H-imidazole-2-methanol.

The compounds identified by Examples 105 to 118, 150, 152, 154, 159 and 161 to 167 are obtained by the same method of preparation as that described in Example 110.

The data for identification of the products 105 to 117 are shown in Table IX.

The data for identification of the products 105, 152, 154, 159, 162 and 163 are shown in Table XI, the data for the products 164 to 167 are shown in Table XII and the data for the products 118 and 161 are shown in Table XIII.

TABLE IX

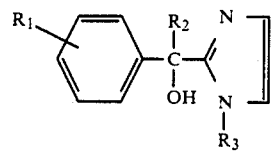

| Example no | R$_1$ | R$_2$ | R$_3$ | M.p. | Recryst. solvent | Method |
|---|---|---|---|---|---|---|
| 105 | H | H | H | 202-3° C. | EtOH/H$_2$O | C |
| 106 | 4 Cl | H | H | 196-7° C. | EtOH/H$_2$O | C |
| 107 | 4 Cl | H | Me | 137-9° C. | MeOH/H$_2$O | C |
| 108 | 3 Cl | H | Me | 126-8° C. | MeOH/H$_2$O | C |
| 109 | 4 F | H | Me | 112-5° C. | MeOH/H$_2$O | C |
| 110 | 3 F$_3$C— | H | Me | 125-6° C. | EtOH/H$_2$O | C |
| 111 | 4 F$_3$C— | H | Me | 124-5° C. | MeOH/H$_2$O | C |
| 112 | 3 4 5 tri MeO | H | Me | 160-1° C. | MeOH/H$_2$O | C |
| 113 | 3 4 di Cl | H | Me | 157-9° C. | EtOH/H$_2$O | C |

TABLE IX-continued

[Structure: R₁-phenyl-C(OH)(R₂)-imidazole with N-R₃]

| Example no | R₁ | R₂ | R₃ | M.p. | Recryst. solvent | Method |
|---|---|---|---|---|---|---|
| 114 | 4 F₃C— | H | n-Bu | 111–2° C. | EtOH/H₂O | C |
| 115 | 2,4 di Cl | H | n-Bu | 94–7° C. | EtOH/H₂O | C |
| 116 | 4 Cl | H | n-Bu | 108–110° C. | Ether/Hexane | C |
| 117 | 3,4,5 tri MeO | H | n-Bu | 122–5° C. | EtOH/H₂O | C |
| 118 | 3,4,5 tri MeO | H | n-dodecyl | oil | — | C |

Method D (Examples 119 et seq.)

Example 121:

Preparation of α-(4-chlorophenyl)-α-methyl-1-methyl-1H-imidazole-2-methanol

A solution of 44 g of α-(4-chlorophenyl)-1-methyl-1H-imidazole-2-methanone in 50 ml of ether is added slowly to a Grignard reagent formed from 10 g of magnesium metal and 57 g of ethyl iodide in ethyl ether. The mixture is refluxed for 3 hours, left to cool and hydrolyzed with an aqueous solution of ammonium chloride.

The product is filtered off, washed with water and recrystallized from an ethanol/water mixture.

This gives 40.1 g (85%) of white crystals melting at 191°–2°, which correspond to α-(4-chlorophenyl)-α-methyl-1-methyl-1H-imidazole-2-methanol.

The compounds identified by Examples 119 to 149 and 169 to 175 are obtained by the same method of preparation as that described in Example 121.

The data for identification of the products 119 to 149 and 169 to 175 are shown in Tables X to XII and the data for the products 148 and 170 are shown in Table XIII.

TABLE X

| Example no | R₁ | R₂ | R₃ | M.p. | Recryst. solvent | Method |
|---|---|---|---|---|---|---|
| 119 | 3 Cl | n-Bu | Me | 125–6° C. | EtOH/H₂O | D |
| 120 | 3 Cl | Me | Me | 180–1° C. | EtOH/H₂O | D |
| 121 | 4 Cl | Me | Me | 191–2° C. | EtOH/H₂O | D |
| 122 | 4 Cl | Me—N(piperidinyl)— | Me | 183–4° C. | AcOEt/Ether | D |
| 123 | 4 Cl | Et | Me | 166–8° C. | EtOH/H₂O | D |
| 124 | 4 Cl | n-Bu | Me | 120–2° C. | EtOH/H₂O | D |
| 125 | 4 Cl | cyclohexyl | Me | 161–2° C. | EtOH | D |
| 126 | 2 Cl | Me | Me | 181–2° C. | EtOH/H₂O | D |
| 127 | 2 Cl | n-Bu | Me | 138–41° C. | Ether | D |
| 128 | 3 F₃C— | Me | Me | 193–4° C. | EtOH/H₂O | D |
| 129 | 3 F₃C— | n-Bu | Me | 140–1° C. | EtOH/H₂O | D |
| 130 | 3 F₃C— | cyclohexyl | Me | 156–7° C. | Heptane/Ether | D |

TABLE X-continued

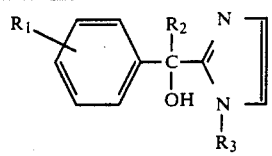

| Example no | R₁ | R₂ | R₃ | M.p. | Recryst. solvent | Method |
|---|---|---|---|---|---|---|
| 131 | 4 F₃C— | Me | Me | 167–8° C. | EtOH/H₂O | D |
| 132 | 4 F | Me | Me | 176–7° C. | EtOH/H₂O | D |
| 133 | 4 Me—O | Me | Me | 181–2° C. | EtOH/H₂O | D |
| 134 | 3,4 di Cl | Me | Me | 207–8° C. | EtOH/H₂O | D |
| 135 | 3,4 di Cl | n-Bu | Me | 142–4° C. | ACN | D |
| 136 | 3,4 di Cl | cyclohexyl | Me | 158–60° C. | ACN/H₂O | D |
| 137 | 3,4,5 tri MeO | CH₃ | Me | 181–2° C. | EtOH/H₂O | D |
| 138 | 4 Cl | Me | n-Bu | 174–5° C. | EtOH | D |
| 139 | 4 Cl | n-Bu | n-Bu | 134–5° C. | ACN | D |
| 140 | 4 Cl | CH₃—N-piperidinyl | n-Bu | 184–5° C. | AcOEt/Ether | D |
| 141 | 3,4,5 tri MeO | n-Bu | n-Bu | 125–6° C. | EtOH/H₂O | D |
| 142 | 2 Cl | n-Bu | n-Bu | 132–3° C. | Ether | D |
| 143 | 3 F₃C | Et | n-Bu | 164–5° C. | EtOH/H₂O | D |
| 144 | 2,4 di Cl | n-Bu | n-Bu | 142–3° C. | ACN/H₂O | D |
| 145 | 4 Cl | Me | piperidinyl-N—(CH₂)₂— | 136–7° C. | EtOH/H₂O | D |
| 146 | 4 Cl | Me | Me₂N—(CH₂)₃— | 147–8° C. | EtOH/H₂O | D |
| 147 | 3,4,5 tri MeO | n-Bu | n-Dodecyl | 75–7° C. | AcOEt | D |
| 148 | 3 F₃C— | n-Bu | φ-CH₂— | oil | — | D |
| 149 | 4 Cl | Me | φ-CH₂— | 154–5° C. | Bz/Ether | D |

ACN = acetonitrile
φ = phenyl
Bz = benzene

TABLE XI

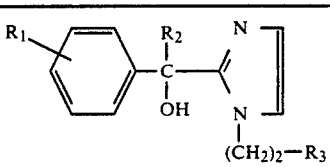

| Example n° | R₁ | R₂ | R₃ | M.p. | Recryst. solvent | Method |
|---|---|---|---|---|---|---|
| 150 | 4 Cl | H | CN | 134–5° C. | EtOH/H₂O | C |
| 151 | 4 Cl | H | NH₂ | 187–8° C. | EtOH/H₂O | I |
| 152 | 3 Cl | H | CO₂H | 212–3° C. | MeOH/H₂O | C |

TABLE XI-continued

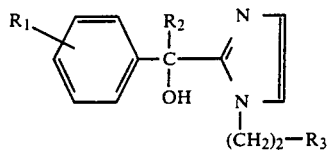

| Example n° | $R_1$ | $R_2$ | $R_3$ | M.p. | Recryst. solvent | Method |
|---|---|---|---|---|---|---|
| 153 | 4 Cl | H | $CH_2OH$ | 121-2° C. | $MeOH/H_2O$ | I |
| 154 | 4 Cl | H | $CO_2Me$ | 96-7° C. | $MeOH/H_2O$ | C |
| 155 | H | H | $CH_2OH$ | 110-1° C. | Ether | I |
| 156 | 4 Me | H | $CH_2OH$ | 104-5° C. | Ether | I |
| 157 | 4 MeO— | H | $CH_2OH$ | oil | — | I |
| 158 | 3 di Cl 4 | H | $CH_2OH$ | 138-9° C. | Ether | I |
| 159 | H | H | $CO_2Me$ | 93-6° C. | $MeOH/H_2O$ | C |
| 160 | 4 Cl | H | $(CH_2)_2$—OH | 131-2° C. | Ether | I |
| 161 | 4 Cl | H | $CH_2$—CN | oil | — | C |
| 162 | 4 Cl | H | $CH_2$—$CO_2H$ | >300° C. | — | C |
| 163 | 4 Cl | H | $CH_2$—$CO_2Me$ | 85-7° C. | Ether | C |

Method E (Examples 164 et seq.)

Example 164:

Preparation of 1-butyl-α-phenyl-1H-pyrazole-5-methanol

A solution of 12.4 g of 1-butylpyrazole in 100 ml of absolute ether is placed in a three-necked flask provided with a stirrer, a condenser, a dropping adapter and a thermometer, it is cooled with ice and 6.1 g of a 1.6M solution of butyllithium in hexane are added slowly. The mixture is stirred for 30 minutes and a solution of 14.5 g of p-chlorobenzaldehyde in 30 ml of absolute ether is added slowly. After the reaction, stirring is continued until the mixture reaches room temperature, after which it is hydrolyzed with 100 ml of water. Extraction is carried out with benzene, the benzene phase is washed and dried over sodium sulfate and the solvent is removed in vacuo.

This gives 18.9 g (82%) of an oil which can be crystallized from a methanol/water mixture to give crystals melting at 46°-7° C., the product being 1-butyl-α-phenyl -1H-pyrazole-5-methanol.

The compounds identified by Examples 164 to 167, 177 and 178 are obtained by the same method of preparation as that which has been described.

The data for identification of these products are shown in Tables XII and XIII.

Method F

Example 168:

Preparation of 4-bromo-1-methyl-α-phenyl-1H-pyrazole-5-methanol

A solution of 0.9 g of bromine in 3 ml of chloroform is added dropwise to a solution of 1 g of α-phenyl-1H-imidazole-2-methanol in 10 ml of chloroform. The mixture is left at room temperature for 4 hours and the solvent is removed in vacuo. The residue is taken up in ethanol and water is added. The product is filtered off and recrystallized from an ethanol/water mixture to give 1.3 g (92%) of yellow crystals of 4-bromo-1,α-dimethyl-1H-pyrazole-5-methanol melting at 110°-111° C.

The data for identification of the products 168 and 176 are given in Table XII.

TABLE XII

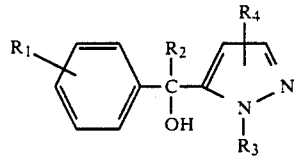

| Example n° | $R_1$ | $R_2$ | $R_3$ | $R_4$ | M.p. | Recryst. solvent | Method |
|---|---|---|---|---|---|---|---|
| 164 | H | H | n-Bu | H | 47-8° C. | $MeOH/H_2O$ | C/E |
| 165 | 4 Cl | H | Me | H | 94-7° C. | $MeOH/H_2O$ | C/E |
| 166 | 3 tri MeO 4 5 | H | Me | H | oil | — | C/E |
| 167 | 3 tri MeO 4 5 | H | n-Bu | H | oil | — | C/E |
| 168 | H | H | Me | 4-Br | 110-11° C. | $EtOH/H_2O$ | F |
| 169 | 4 Cl | φ | Me | H | 167-8° C. | Bz/ACN | D |
| 170 | 4 Cl | Me | n-Bu | H | oil | — | D |
| 171 | H | Me | Me | H | 99-100° C. | Ether/Hex | D |
| 172 | 3 tri MeO 4 5 | Me | Me | H | 144-5° C. | Bz/Ether | D |
| 173 | H | Me | Me | 3 Me | 137-8° C. | $EtOH/H_2O$ | D |

TABLE XII-continued

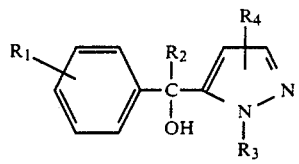

| Example n° | R₁ | R₂ | R₃ | R₄ | M.p. | Recryst. solvent | Method |
|---|---|---|---|---|---|---|---|
| 174 | H | CH₂=CH— | Me | H | 95–6° C. | Ether/Pen | D |
| 175 | 4 Cl | CH₂=CH— | n-Bu | H | 84–5° C. | Ether/Pen | D |
| 176 | H | H | Me | 4 Cl | oil | — | F |
| 177 | 2-Me | H | Me | H | 113–4° C. | EtOH/H₂O | C/E |
| 178 | 3 Cl | H | Me | H | 128–9° C. | Ether | C/E |
| 179 | 4 Me | H | Me | H | 123–6° C. | Ether | C |
| 180 | 2 Cl | H | Me | H | 96–8° C. | Ether | C |
| 181 | 4 MeO | H | Me | H | 129–30° C. | Ether | C |

Hex = hexane
Pen = pentane
Bz = benzene
φ = phenyl

Method G (Examples 182 et seq.)

Example 182:

Preparation of α-(4-chlorophenyl)-α-methyl-1-methyl-0(2-trimethylammonioethyl) -1H-imidazole-2-methanol iodide A solution of 2.9 g of α-(4-chlorophenyl)-α-methyl-1-methyl-1H-imidazole-2-methanol and 1.3 g of methyl iodide in 20 ml of acetone is heated at 70° C. for 70 hours in a closed vessel. It is cooled and the solvent is removed in vacuo to give 4.2 g (100% yield) of α-(4-chlorophenyl)-α-methyl-1-methyl-0-(2-trimethylammonioethyl) -1H-imidazole-2-methanol iodide melting at 55° C.

The compounds identified by Examples 182 to 185 are obtained by the same method of preparation as that which has been described.

The data for identification of the products 182 to 185 are shown in Tables XIV and XV.

Method H

Example 186:

Preparation of α-(4-methoxyphenyl)-α-methyl-1,1-dimethylimidazolio-2-methanol iodide A solution of 1.4 g of α-(4-methoxyphenyl)-α-methyl -1-methyl-1H-imidazole-2-methanol and 0.9 g of methyl iodide in 30 ml of acetone is heated at 60° C. for 48 hours in a closed vessel. It is cooled and evaporated in vacuo to give 2.2 g of α-(4-methoxyphenyl)-α-methyl-1,1-dimethylimidazolio-2-methanol iodide melting at 45° C.

The data for identification of this product are shown in Tables XIV and XV.

Method I (Examples 151, 153, 155 et seq.)

Example 153:

Preparation of 1-(4-hydroxypropyl)-α-(4-chlorophenyl)-1H-imidazole-2-methanol

Lithium aluminum hydride (0.8 g, 0.02 mol) is added cautiously to a solution of 1-(3-methoxycarbonylethyl) -α-(4-chlorophenyl)-1H-imidazole-2-methanone (2.9 g, 0.01 mol) in ether (100 ml) and the mixture is refluxed for 3 hours.

The ether is evaporated off, the residue is taken up with chloroform and the solution is washed with water, dried and evaporated to give 1.8 g of product, which is recrystallized from a methanol/water mixture.

The compounds identified by Examples 155 to 158 and 160 are obtained by the same method, the data for their identification are shown in Table XI and the data for the product 157 are shown in Table XIII.

TABLE XIII

| Example n° | ¹H NMR-Cl₃CD |
|---|---|
| 118 | 6.8 (d,2H); 6.5 (s,2H); 4,6 (b,1H); 3,7 (m,11H); 2,4 (m,2H); 1,5–0,6 (m,22H) |
| 148 | 7,9–6,1 (m,10H); 4,9 (m,1H); 2.5 (t,2H); 1,5–0,5 (m,9H) |
| 161 | 8,0 (b,1H); 7,2 (s,4H); 6.8 (s,1H); 5,9 (s,1H); 5,2 (s,1H); 4,8 (t,2H); 2,3–1,6 (m,4H) |
| 166 | 7,3 (d,1H); 6,5 (s,2H); 5,9 (s,1H); 5,7 (s-1H); 3.6 (m,12H) |
| 167 | 7.2 (d,1H); 6.5 (s.2H); 5,9 (s,1H); 5,7 (s,1H); 3.7 (m,11H); 1.7–0.4 (m,7H) |
| 176 | 7.3 (s,6H); 5.8 (s,1H); 3.6 (m,5H); 2,6 (t,2H); 2.3 (s,6H) |

TABLE XIV

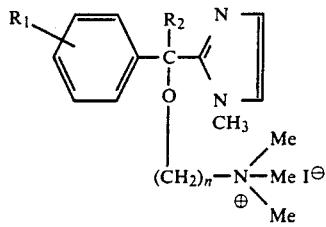

| Example n° | $R_1$ | $R_2$ | H | M.p. | Yield | Method |
|---|---|---|---|---|---|---|
| 182 | 4 Cl | Me | 2 | 55 | Quant. | G |
| 183 | 4 Cl | Me | 3 | 60 | Quant. | G |
| 184 | 4 MeO | Me | 2 | 50 | Quant. | G |
| 185 | 4 MeO | Me | 3 | 50 | Quant. | G |
| 186 | 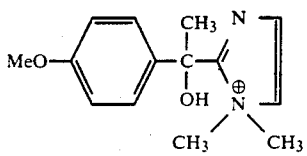 | | | 45 | Quant. | H |

TABLE XV

| Pat n° | $^1$H NMR-Cl$_3$CD |
|---|---|
| 182 | 7,2 (q,4H); 6,9 (d,2H); 4,1 (m,2H); 3,6 (s,9H); 3,4 (m,2H); 3,25 (s,3H); 2,0 (s,3H) |
| 183 | 7,25 (q,4H); 6,9 (d,2H); 3,8 (m,2H); 3,5 (s,9H); 3,2 (s,3H); 3,1 (m,2H); 2,2 (m,2H); 1,8 (s,3H) |
| 184 | 6,9 (m,6H); 4,1 (m,2H); 3,8 (s,3H); 3,6 (s,9H); 3,3 (m,2H); 3,2 (s,3H); 1,9 (s,3H) |
| 185 | 7,3–6,7 (m,6H); 3,8 (m,5H); 3,4 (s,9H); 3,2 (m,5H); 2,15 (m,5H) |
| 186 | 8,0–6,8 (m,6H); 4,0 (s,3H); 3,8 (m,3H) |

Analgesic activity: Inhibition of the contortions induced by acetylcholine bromide in mice—Collier's method (H. O. W. Collier, L. C. Dinneen, C. A. Johnson and C. Schneider, Br. J. Pharmac. Chemother., 32, 295 (1968))

Swiss male mice weighing 17–22 grams are used. Groups containing a minimum of 4 animals are used.

Contortions are induced by the intraperitoneal injection of acetylcholine bromide (7.2 mg/kg, dissolved in physiological serum, a volume of 10 ml/kg of weight being administered) at the start of the experiment and the number of contortions is counted for 5 minutes, this being the reference number for each animal (mice with fewer than 2 contortions are rejected). Immediately afterwards, the test products are administered orally, at a dose of 160 mg/kg, in the form of a suspension or solution in gum arabic at a concentration of 5% (w/v) in distilled water. 40 and 120 minutes after the treatment, acetylcholine bromide is administered again, the contortions are noted and the readings at 40 and 120 minutes are evaluated, taking the contortions of the initial reading as the reference. The mean of the values at 40 and 120 minutes gives the percentage inhibition of the contortions, which defines the analgesic activity of the test products.

The results obtained with some of the products described are summarized in Table XVI.

TABLE XVI

Analgesic activity: Inhibition of the contortions induced by acetylcholine bromide in mice
Dose of product: 160 mg/kg, administered orally

| Product | % inhibition of contortions |
|---|---|
| 2 | 100.0 |
| 4 | 95.0 |
| 5 | 100.0 |
| 6 | 75.0 |
| 7 | 95.0 |
| 8 | 95.0 |
| 9 | 97.5 |
| 14 | 85.0 |
| 59 | 100.0 |
| 60 | 82.5 |
| 61 | 97.5 |
| 64 | 100.0 |
| 68 | 95.0 |
| 69 | 95.0 |
| 70 | 100.0 |
| 72 | 100.0 |
| 73 | 100.0 |
| 74 | 100.0 |
| 75 | 100.0 |
| 76 | 100.0 |
| 77 | 100.0 |
| 78 | 100.0 |
| 82 | 83.8 |
| 83 | 88.3 |
| 107 | 57.5 |
| 110 | 57.5 |
| 111 | 87.5 |
| 117 | 60.0 |
| 119 | 90.0 |
| 121 | 70.0 |
| 126 | 65.0 |
| 127 | 70.0 |
| 128 | 82.5 |
| 129 | 55.0 |
| 133 | 52.5 |
| 137 | 85.0 |
| 141 | 62.5 |
| 142 | 80.0 |
| 144 | 88.8 |
| Acetylsalicylic acid | 92.5 |
| Paracetamol | 72.5 |
| Nefopam | 100.0 |

Analgesic activity: Inhibition of the contortions induced by phenylbenzoquinone in mice—Siegmund's method (E. Siegmund, R. Cadmus and G. Lu, *Proc Soc. Exp. Biol. Med.*, 95, 729 (1957))

Swiss male mice weighing 17-22 grams are used. Groups containing a minimum of 4 animals are used.

Contortions are induced by the intraperitoneal injection of phenyl-p-benzoquinone (25 ml/kg of a 0.02% solution in a solution of ethanol at a concentration of 5% (v/v) in distilled water, with Evans blue in a proportion of 0.1% (w/v)) and are counted for 15 minutes as from the time of injection. Each product is suspended or dissolved in gum arabic at a concentration of 5% (w/v) in distilled water and is administered orally, at a dose of 160 mg/kg, 60 minutes before the injection of phenylbenzoquinone. The inhibition of contortions due to each product is determined, taking as the reference the contortions in a group of control animals to which only the vehicle is administered orally 60 minutes before the phenylbenzoquinone.

The results obtained with some of the products described are summarized in Table XVII.

TABLE XVII

Analgesic activity: Inhibition of the contortions induced by phenylbenzoquinone in mice
Dose of product: 160 mg/kg, administered orally

| Product | % inhibition of contortions |
|---|---|
| 18 | 82.5 |
| 19 | 87.5 |
| 20 | 25.0 |
| 27 | 40.0 |
| 30 | 27.5 |
| 31 | 80.0 |
| 32 | 37.5 |
| 33 | 35.0 |
| 34 | 40.0 |
| 37 | 77.5 |
| 38 | 42.5 |
| 39 | 37.5 |
| 86 | 98.8 |
| 87 | 77.5 |
| 91 | 57.5 |
| 94 | 40.0 |
| 95 | 45.0 |
| 113 | 57.5 |
| 115 | 39.5 |
| 116 | 27.5 |
| 128 | 67.5 |
| 146 | 28.5 |
| Acetylsalicylic acid | 75.0 |
| Paracetamol | 47.5 |
| Nefopam | 97.5 |

Analgesic activity: Inhibition of the contortions induced by acetic acid in mice—Koster's method (R. Koster. M. Anderson and E. J. De Beer, *Fed. Proc.*, 18, 412 (1959))

Swiss male mice weighing 17-22 grams are used. Groups containing a minimum of 4 animals for each dose are used.

Contortions are induced by the intraperitoneal injection of acetic acid (25 ml/kg of a solution of 5.25 mg/ml of acetic acid in distilled water, with Evans blue in a proportion of 0.1% (w/v)) and are counted for 15 minutes as from the time of injection. Each product is suspended or dissolved in gum arabic at a concentration of 5% (w/v) in distilled water and is administered orally, at a dose of 160 mg/kg, 60 minutes before the injection of acetic acid. The inhibition of contortions due to each product is determined, taking as the reference the contortions in a group of control animals to which only the vehicle is administered orally 60 minutes before the acetic acid.

The results obtained with some of the products described are summarized in Table XVIII.

TABLE XVIII

Analgesic activity: Inhibition of the contortions induced by acetic acid in mice
Dose of product: 160 mg/kg, administered orally

| Product | % inhibition of contortions |
|---|---|
| 6 | 50.0 |
| 7 | 67.5 |
| 12 | 82.5 |
| 31 | 80.0 |
| 37 | 72.5 |
| 59 | 87.5 |
| 60 | 62.5 |
| 64 | 50.0 |
| 86 | 50.0 |
| 115 | 50.0 |
| 119 | 45.0 |
| 128 | 52.5 |
| Acetylsalicylic acid | 72.5 |
| Paracetamol | 20.0 |
| Nefopam | 98.0 |

On account of their good pharmacodynamic properties, the arylheteroarylcarbinol derivatives according to the invention can be used satisfactorily in human and animal therapy, in particular in the treatment of pain of moderate to high intensity, for example: sciatica, lumbago, dorsalgia, sprains, fractures, dislocations, all kinds of postoperative pain and pain of dental origin.

In human therapy, the dose at which the derivatives of the present invention are administered depends of course on the severity of the complaint to be treated. It will generally be between about 90 and about 270 mg/day. The derivatives of the invention will be administered for example in the form of tablets or injectable solutions or suspensions.

Two particular pharmaceutical forms of the derivatives forming the subject of the present invention are now indicated below as examples:

| Example of formulation per tablet | |
|---|---|
| 1-Methyl-0-(2-dimethylaminoethyl)-1H-pyrazole-5-methanol citrate | 30.00 mg |
| Lactose | 119.50 mg |
| Cornstarch | 46.00 mg |
| Microcrystalline cellulose | 23.00 mg |
| Povidone K-90 | 4.60 mg |
| Pregelatinized starch | 4.60 mg |
| Colloidal silicon dioxide | 1.15 mg |
| Magnesium stearate | 1.15 mg |
| Weight of tablet | 230.00 mg |
| Example of formulation per injectable ampoule | |
| 1-Methyl-0-(2-dimethylaminoethyl)-1H-pyrazole-5-methanol citrate | 20.00 mg |
| Dextrose | 50.00 mg |
| Water for injection, q.s. | 1.00 mg |

What is claimed is:

1. An arylheteroarylcarbinol derivative corresponding to formula I:

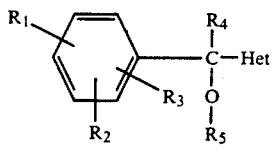

or a therapeutically acceptable salt, in which formula:
each $R_1$, $R_2$ and $R_3$ separately represents a member selected from the group consisting of the hydrogen atom, a halogen, a lower alkyl radical, a lower alkoxy radical and a trifluoro-methyl group,
$R_4$ represents a member selected from the groups consisting of the hydrogen atom, a $C_1$ to $C_4$ lower alkyl radical, a cycloalkyl radical, a lower alkenyl radical and a cycloalkylamino radical substituted on the nitrogen atom,
$R_5$ represent a member selected from the group consisting of the hydrogen atom and radicals of the formula:

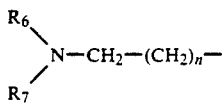

in which n can have the value 1 or 2 and the group:

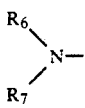

is a member selected from the group consisting of lower dialkylamino groups and pyrrolidino group, or
$R_5$ represents a group of formula:

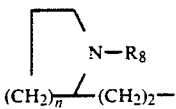

in which is 1 in which $R_8$ is a lower alkyl group, and
Het represents a pyrazole of formula:

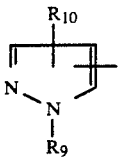

in which $R_9$ is selected from the class consisting of the hydrogen atom, $C_1$ to $C_4$ lower alkyl radicals, the dodecyl radical and the benzyl radical and
$R_{10}$ represents a member of the class consisting of the hydrogen atom, methyl radicals and halogen atoms.

2. A compound corresponding to formula I as claimed in claim 1, which is selected from the group consisting of:

1-butyl-αphenyl-0-(2-dimethylaminoethyl)-1H-pyrazole-5-methanol,
α-(4-chlorophenyl)-1-methyl-α-phenyl-0-(2-dimethylaminoethyl) -1H-pyrazole-5-methanol,
1-butyl-α-(3,4,5-trimethoxyphenyl)-0-(2-dimethylaminoethyl) -1H-pyrazole-5-methanol,
1-butyl-α-(4-chlorophenyl)-α-methyl-0-(2-dimethylaminoethyl) -1H-pyrazole-5-methanol,
1-methyl-αphenyl-0-(2-dimethylaminoethyl)-1H-pyrazole-5-methanol,
α-methyl-1-αphenyl-1-methyl-0-(2-dimethylaminoethyl)-1H-pyrazole -5-methanol,
1-methyl-α-(3,4,5-trimethoxyphenyl)-0-(2-dimethylaminoethyl) -1H-pyrazole-5-methanol,
1-methyl-αphenyl-0-[ethyl-2-(1-pyrrolidone)]-1H-pyrazole-5-methanol,
α-methyl-1-methyl-α-(3,4,5-trimethoxyphenyl)-0-(2-dimethylaminoethyl) -H-pyrazole-5-methanol,
4-bromo-1-methyl-αphenyl-0-(2-dimethylaminoethyl)-1H-pyrazole-5-methanol,
1,3-dimethyl-α-methyl-αphenyl-0-(2-dimethylaminoethyl)-1H-pyrazole-5-methanol,
1,3-dimethyl-αphenyl-0-(2-dimethylaminoethyl)-1H-pyrazole-5-methanol,
1-methyl-α-(2-methylphenyl)-0-(2-dimethylaminoethyl) -1H-pyrazole-5-methanol,
1-methyl-4-chloro-α-(4-chlorophenyl)-0-(2-dimethylaminoethyl) -1H-pyrazole-5-methanol,
1-methyl-α-(4-chlorophenyl)-0-(2-dimethylaminoethyl) -1H-pyrazole-4-methanol,
1-methyl-α-methyl-α-(4-chlorophenyl)-0-(2-dimethylaminoethyl) -1H-pyrazole-4-methanol,
1-methyl-α-(4-chlorophenyl)-0-(2-dimethylaminoethyl) -1H-pyrazole-5-methanol,
1-methyl-α-(3-chlorophenyl)-0-(2-dimethylaminoethyl) -1H-pyrazole-5-methanol,
1-methyl-α-(4-methylphenyl)-0-(2-dimethylaminoethyl) -1H-pyrazole-5-methanol,
1-methyl-α-(2-chlorophenyl)-0(2-dimethylaminoethyl) -1H-pyrazole-5-methanol,
1-methyl-α-phenyl-0[2-(N-methylpyrrolidin-2-yl)-ethyl]-1H-pyrazole-5-methanol,
1-methyl-α-phenyl-0(2-diisopropylaminoethyl)-1H-pyrazole-5-methanol,
1-methyl-α-(4-chlorophenyl)-0-(2-diisopropylaminoethyl) -1H-pyrazole-4-methanol,
1-methyl-α-(4-chlorophenyl)-0[2-(N-methylpyrrolidin-2-yl)ethyl]-1H-pyrazole-4methanol,
1-butyl-αphenyl-0-(3-dimethylaminopropyl)-1H-pyrazole-5-methanol,
1-butyl-α-(4-chlorophenyl)-α-methyl-0-(3-dimethylaminopropyl) -1H-pyrazole-5-methanol,
1-methyl-αphenyl-0-(3-dimethylaminopropyl)-1H-pyrazole-5-methanol,
1-methyl-α-methyl-αphenyl-0-(3-dimethylaminopropyl)-1H-pyrazole-5-methanol,
1-3-dimethyl-α-methyl-αphenyl-0-(3-dimethylaminopropyl)-1H-pyrazole -5-methanol,
1,3-dimethyl-αphenyl-0-(3-dimethylaminopropyl)-1H-pyrazole-5methanol,
1-methyl-α-(2-methylphenyl)-0-(3-dimethylaminopropyl) -1H-pyrazole-5methanol,
1-methyl-α-(4-chlorophenyl)-0-(3-dimethylaminopropyl)-1H-pyrazole-5methanol,
1-methyl-α-phenyl-0-(3-dimethylaminopropyl)-1H-pyrazole-4-methanol,
1-methyl-α-(4-chlorophenyl)-0(propyl-3-N-pyrrolidine)-1H-pyrazole-4methanol, 1-methyl-α-phenyl-0-(propyl-3-N-pyrrolidine)-1H-pyrazole-5methanol,
1-butyl-α-phenyl-1H-pyrazole-5-methanol,
α-(4-chlorophenyl)-1-methyl-1H-pyrazole-5methanol,
1-methyl-α-(3,4,5-trimethoxyphenyl)-1H-pyrazole-5-methanol,
1-butyl-α-(3,4,5-trimethoxyphenyl)-1H-pyrazole-5methanol,
4-bromo-1-methyl-α-phenyl-1H-pyrazole-5-methanol,
α-(4-chlorophenyl)-1-methyl-α-phenyl-1H-pyrazole-5-methanol,
1-butyl-α-(4-chlorophenyl)-α-methyl-1H-pyrazole-5-methanol,
1-methyl-α-methyl-α-phenyl-1H-pyrazole-5-methanol,
1-methyl-α-methyl-α-(3,4,5-trimethoxyphenyl)-1H-pyrazole-5-methanol,
1,3-dimethyl-α-methyl-α-phenyl-1H-pyrazole-5-methanol,
α-ethenyl-1methyl-α-phenyl-1H-pyrazole-5-methanol,
1-butyl-α-(4-chlorophenyl)-α-ethenyl-1H-pyrazole-5methanol,
4-chloro-1-methyl-α-phenyl-1H-pyrazole-5-methanol,
1-methyl-α-(2-methylphenyl)-1H-pyrazole-5-methanol,
1-methyl-α-(3-chlorophenyl)-1H-pyrazole-5-methanol,
1-methyl-α-(4-methylphenyl)-1H-pyrazole-5-methanol,
1-methyl-α-(2-chlorophenyl)-1H-pyrazole-5-methanol and
1-methyl-α-(4-methoxyphenyl)-1H-pyrazole-5-methanol.

3. Pharmaceutical compositions which contain, in addition to a pharmaceutically acceptable excipient, an analgesically effective amount of at least one derivative of formula I or one of its physiologically acceptable salt as claimed in one of claims 1 or 2.

4. A method for treating a person in pain which comprises administering to said patient an analgesically effective amount of at least one derivative of formula I as set forth in claim 1, or a physiologically acceptable salt thereof.

5. A compound corresponding to formula I as claimed in claim 1, which is selected from the group consisting of:
1-butyl-α-phenyl-0-(2-dimethylaminoethyl)-1H-pyrazole-5methanol,
α-(4-chlorophenyl)-1-methyl-α-phenyl-0-(2-dimethylaminoethyl) -1H-pyrazole-5-methanol,
1-butyl-α-(3,4,5-trimethoxyphenyl)-0-(2-dimethylaminoethyl) -1H-pyrazole-5-methanol,
1-butyl-α-(4-chlorophenyl)-α-methyl-0-(2-dimethylaminoethyl) -1H-pyrazole-5-methanol,
1-methyl-αphenyl-0-(2-dimethylaminoethyl)-1H-pyrazole-5methanol,
α--methyl-1-αphenyl-1-methyl-0-(2-dimethylaminoethyl)-1H-pyrazole-5methanol,
1-methyl-α-(3,4,5-trimethoxyphenyl)-0-(2-dimethylaminoethyl) -1H-pyrazole-5methanol,
1-methyl-αphenyl-0-[ethyl-2-(1-pyrrolidone)]-1H-pyrazole-5-methanol,
α-methyl-1-methyl-α-(3,4,5-trimethoxyphenyl)-0-(2-dimethylaminoethyl) -H-pyrazole-5methanol,
4-bromo-1-methyl-αphenyl-0(2-dimethylaminoethyl)-1H-pyrazole-5-methanol,
1,3-dimethyl-α-methyl-αphenyl-0-(2-dimethylaminoethyl)-1H-pryazole-5-methanol,
1,3-dimethyl- phenyl-0-(2-dimethylaminoethyl)-1H-pyrazole-5-methanol,
1-methyl- -(2-methylphenyl)-0-(2-dimethylaminoethyl) -1H-pyrazole-5-methanol,
1-methyl-4-chloro-α-(4-chlorophenyl)-0-(2-dimethylaminoethyl) -1H-pyrazole-5-methanol,
1-methyl-α-(4-chlorophenyl)-0-(2-dimethylaminoethyl) -1H-pyrazole-4-methanol,
1-methyl-α-methyl-α-(4-chlorophenyl)-0-(2-dimethylaminoethyl) -1H-pyrazole-4-methanol,
1-methyl-α-(4-chlorophenyl)-0-(2-dimethylaminoethyl) -1H-pyrazole-5methanol,
1-methyl-α-(3-chlorophenyl)-0-(2-dimethylaminoethyl) -1H-pyrazole-5-methanol,
1-methyl-α-(4-methylphenyl)-0-(2-dimethylaminoethyl) -1H-pyrazole-5-methanol,
1-methyl-α-(2-chlorophenyl)-0-(2-dimethylaminoethyl) -1H-pyrazole-5-methanol,
1-methyl-α-phenyl-0-[2-(N-methylpyrrolidin-2-yl)-ethyl]-1H-pyrazole-5-methanol,
1-methyl-α-phenyl-0(2-diisopropylaminoethyl)-1H-pyrazole-5-methanol,
1-methyl-α-(4-chlorophenyl)-0-(2-diisopropylaminoethyl) -1H-pyrazole-4-methanol,
1-methyl-α-(4-chlorophenyl)-0-[2-(N-methylpyrrolidin-2yl)ethyl]-1H-pyrazole-4-methanol,
1-butyl-phenyl-0-(3-dimethylaminopropyl)-1H-pyrazole-5-methanol,
1-butyl-α-(4-chlorophenyl)-α-methyl-0(3-dimethylaminopropyl) -1H-pyrazole-5-methanol,
1-methyl-αphenyl-0-(3-dimethylaminopropyl)-1H-pyrazole-5-methanol,
1-methyl-α-methyl-αphenyl-0-(3-dimethylaminopropyl)-1H-pyrazole-5methanol,
1-3-dimethyl-α-methyl-αphenyl-0-(3-dimethylaminopropyl)-1H-pryazole-5-methanol,
1,3-dimethyl-αphenyl-0-(3-dimethylaminopropyl)-1H-pyrazole-5-methanol,
1-methyl-α-(2-methylphenyl)-0-(3-dimethylaminopropyl) -1H-pyrazole-5-methanol,
1-methyl-α-(4-chlorophenyl)-0-(3-dimethylaminopropyl) -1H-pyrazole-5-methanol,
1-methyl-α-phenyl-0-(3-dimethylaminopropyl)-1H-pyrazole-4-methanol,
1-methyl-α-(4-chlorophenyl)-0-(propyl-3-N-pyrrolidine)-1H-pyrazole-4-methanol,
1-methyl-α-phenyl-0-(propyl-3-N-pyrrolidine)-1H-pyrazole-5-methanol,
1-butyl-α-phenyl-1H-pyrazole-5-methanol,
α-(4-chlorophenyl)-1-methyl-1H-pyrazole-5-methanol,
1-methyl-α-(3,4,5-trimethoxyphenyl)-1H-pyrazole-5-methanol,
1-butyl-α-(3,4,5-trimethoxyphenyl)-1H-pyrazole-5-methanol,
4-bromo-1-methyl-α-phenyl-1H-pyrazole-5-methanol,
α-(4-chlorophenyl)-1-methyl-α-phenyl-1H-pyrazole-5-methanol,
1-butyl-α-(4-chlorophenyl)-α-methyl-1H-pyrazole-5-methanol, 1-methyl-α-methyl-α-phenyl-1H-pyrazole-5-methanol, 1-methyl-α-methyl-α-(3,4,5-trimethoxyphenyl)-1H-pyrazole-5methanol, 1,3,-dimethyl-α-methyl-α-phenyl-1H-pyrazole-5-methanol, α-ethenyl-1-methyl-α-phenyl-1H-pyrazole-5methanol, 1-butyl-α-(4-chlorophenyl)-α-ethenyl-1H-pyrazole-5-methanol, 4-chloro-1-methyl-α-phenyl-1H-pyrazole-5-methanol, 1-methyl-α-(2-methylphenyl)-1H-pyrazole-5-methanol, 1-methyl-α-(3-chlorophenyl)-1H-pyrazole-5-methanol, 1-methyl-α-(4-methylphenyl)-1H-pyrazole-5-methanol, 1-methyl-α-(2-chlorophenyl-1H-pyrazole-5-methanol and 1-methyl-α-(4-methoxyphenyl)-1H-pyrazole-5-methanol.

6. 1-methyl-phenyl-0-(2dimethylaminoethyl)-1H-pyrazole-5-methanol.

7. An arylheteroarylcarbinol derivative corresponding to formula I:

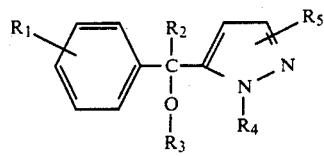

or a therapeutically acceptable salt in which formula:
$R_1$ represents the hydrogen atom, a halogen, a lower alkyl or a lower alkoxy radical,
$R_2$ represents the hydrogen atom, a lower alkyl radical or a cycloalkyl radical,
$R_3$ represents a member selected from the group consisting of the hydrogen atom, a radical of the formula:

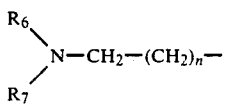

in which n can have the value 1 or 2 and $R_6$ and $R_7$ represent a lower alkyl radical or form together a cycloalkyl radical and a cycloalkoxy radical or $R_3$ represents

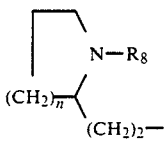

in which n is 1 and $R_8$ represents a lower alkyl radical,
$R_4$ represents a lower alkyl radical, and
$R_5$ represents the hydrogen atom, a halogen or a lower alkyl radical.

* * * * *

UNITED STATES PATENT AND TRADEMARK OFFICE
CERTIFICATE OF CORRECTION

PATENT NO. : 5,017,596
DATED : May 21, 1991
INVENTOR(S) : Augusto Colombo et al.

It is certified that error appears in the above-identified patent and that said Letters Patent is hereby corrected as shown below:

Title page,
Item [75], Inventors, after "Pares" delete "both" and insert -- Jordi Frigola, all --

Signed and Sealed this

Twenty-ninth Day of June, 2004

JON W. DUDAS
*Acting Director of the United States Patent and Trademark Office*